United States Patent
Francis et al.

(10) Patent No.: US 9,913,977 B2
(45) Date of Patent: *Mar. 13, 2018

(54) PROCESS AND SYSTEM FOR IONTOPHORETIC WRINKLE REDUCTION

(71) Applicant: University Medical Pharmaceuticals Corp., Irvine, CA (US)

(72) Inventors: Raymond J. Francis, Irvine, CA (US); John Trengrove, Irvine, CA (US); Gregory Hunt, Irvine, CA (US); Josh Hoyt, Portland, OR (US); Jim Thorne, Portland, CA (US); Darrick Carter, Seattle, OR (US)

(73) Assignee: University Medical Pharmaceuticals Corp., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/298,190

(22) Filed: Jun. 6, 2014

(65) Prior Publication Data
US 2014/0288527 A1 Sep. 25, 2014

Related U.S. Application Data

(63) Continuation of application No. 12/970,224, filed on Dec. 16, 2010, now Pat. No. 8,747,383.
(Continued)

(51) Int. Cl.
*A61M 31/00* (2006.01)
*A61N 1/30* (2006.01)
(Continued)

(52) U.S. Cl.
CPC ............... *A61N 1/30* (2013.01); *A45D 44/22* (2013.01); *A61N 1/22* (2013.01); *A61N 1/328* (2013.01)

(58) Field of Classification Search
CPC .......... A61N 1/30; A61N 1/328; A61N 1/303; A61N 1/32
(Continued)

(56) References Cited

U.S. PATENT DOCUMENTS

| 4,372,296 A | 2/1983 | Fahim |
|---|---|---|
| 4,406,658 A | 9/1983 | Lattin et al. |

(Continued)

FOREIGN PATENT DOCUMENTS

| JP | 1997-9169617 | 6/1997 |
|---|---|---|
| KR | 20-0327534 | 9/2003 |

(Continued)

OTHER PUBLICATIONS

Office Action dated Jan. 23, 2015 in Russian Application 2012130389 including translation in 8 pages.
(Continued)

*Primary Examiner* — Edelmira Bosques
(74) *Attorney, Agent, or Firm* — Orrick, Herrington & Sutcliffe LLP

(57) ABSTRACT

A method and related systems and apparatus for wrinkle reduction. The method includes the steps of positioning and applying a patch to skin of a consumer and adhesively securing the patch to the skin. A chemical composition on the patch includes both active ingredients and adhesive. A pair of electrodes are connected to a battery-driven, microprocessor-based controller. A current is applied through the electrodes in the patch for a selected time. The chemical composition in the patch is propelled into the consumer through use of the current in order to relax the skin or the consumer. The patch is removed and any residue of the chemical composition is massaged into the skin.

20 Claims, 7 Drawing Sheets

Related U.S. Application Data

(60) Provisional application No. 61/288,088, filed on Dec. 18, 2009.

(51) Int. Cl.
*A45D 44/22* (2006.01)
*A61N 1/22* (2006.01)
*A61N 1/32* (2006.01)

(58) Field of Classification Search
USPC .......................................................... 604/501
See application file for complete search history.

(56) References Cited

U.S. PATENT DOCUMENTS

| | | | |
|---|---|---|---|
| 4,702,732 A * | 10/1987 | Powers | A61K 41/00 |
| | | | 29/592.1 |
| 4,979,938 A | 12/1990 | Stephen et al. | |
| 5,505,949 A * | 4/1996 | Benitez | A61K 8/368 |
| | | | 424/401 |
| 5,882,677 A * | 3/1999 | Kupperblatt | A61K 9/0009 |
| | | | 424/443 |
| 6,064,908 A * | 5/2000 | Muller | A61N 1/30 |
| | | | 604/20 |
| 6,123,701 A * | 9/2000 | Nezhat | A61B 18/1442 |
| | | | 600/564 |
| 6,175,763 B1 | 1/2001 | Sorenson et al. | |
| 6,823,202 B2 | 11/2004 | Hause, Jr. | |
| 6,866,856 B2 | 3/2005 | Lu et al. | |
| 7,427,273 B2 | 9/2008 | Mitsui | |
| 7,479,133 B2 | 1/2009 | Sun et al. | |
| 8,747,383 B2 | 6/2014 | Francis et al. | |
| 2004/0167461 A1 | 8/2004 | Nitzan et al. | |
| 2004/0267189 A1 | 12/2004 | Mavor | |
| 2005/0015042 A1 | 1/2005 | Sun et al. | |
| 2006/0100567 A1 | 5/2006 | Marchitto et al. | |
| 2006/0167403 A1 | 7/2006 | Henley et al. | |
| 2007/0092571 A1 * | 4/2007 | Schur | A61K 8/8176 |
| | | | 424/486 |
| 2007/0276451 A1 | 11/2007 | Rigaux | |
| 2009/0048556 A1 | 2/2009 | Durand | |
| 2009/0149800 A1 | 6/2009 | Durand | |
| 2009/0299267 A1 | 12/2009 | Durand | |
| 2010/0286590 A1 | 11/2010 | Durand | |

FOREIGN PATENT DOCUMENTS

| | | |
|---|---|---|
| KR | 20-0403033 | 12/2005 |
| RU | 2373941 | 11/2009 |
| WO | WO 96/36394 | 11/1996 |

OTHER PUBLICATIONS

U.S. Appl. No. 13/834,693, filed Mar. 15, 2013, Francis et al.
Extended European Search Report re App No. PCT/US2010061029 dated Jun. 28, 2013 in 6 pages.
International Search Report dated Aug. 31, 2011 PCT/US2010/061029 in 4 pages.

* cited by examiner

PROCESS AND SYSTEM FOR IONTOPHORETIC WRINKLE REDUCTION

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

This application is a continuation of U.S. patent application Ser. No. 12/970,224 filed Dec. 16, 2010, which claims priority to U.S. Provisional Patent Application Ser. No. 61/288,088, filed Dec. 18, 2009, both are incorporated in their entireties herein by reference.

BACKGROUND OF THE INVENTION

Field of the Invention

The present invention relates and is directed to a process or method of use and a system including a disposable patch to treat wrinkles and fine lines with a chemical composition administered by iontophoresis.

Prior Art

There are various known procedures and various known chemical compositions for treating, reducing or preventing fine lines or wrinkles of the facial skin. It is known that moisturizers containing amino acids play a significant role in skin care by increasing skin elasticity and smoothing the skin. In addition, anti-aging active agents are known to change the skin condition by smoothing and tightening.

Chemical compositions may be administered topically, such as lotions, or administered through transdermal patches. Additionally, chemical compositions may be administered by direct injection. Chemical compositions presently available include those which moisturize the outer skin or epidermis. Other compositions tend to promote cell growth in the skin. Other treatments of wrinkles and fine lines include botulinum toxin (marketed under the trademark Botox®) which inhibits neurotransmission in nerve cells, thereby causing contracted muscles to relax.

In order to increase the speed and effectiveness of delivery of chemical compositions for treatment, it is known to utilize sonic vibrations. For example, Fahim (U.S. Pat. No. 4,372,296) discloses topical treatment of acne with zinc salt and ascorbic acid in a pharmaceutical carrier which is applied with ultra sonic vibrations.

Stephen et al. (U.S. Pat. No. 4,979,938) disclose a method of treating acne using an applicator electrode having a solution capable of producing hydroxyl ions. An applicator electrode is placed against the skin and a voltage differential is applied to produce and drive hydroxyl ions into the skin tissue.

Sun et al. (U.S. Pat. No. 7,479,133) discloses a device for treating acne or rosacea by applying an electrical charge with two conductive electrodes in communication with a carrier containing an electrolyte.

More recently, the Durand patent publications (U.S. Patent Publication No. 2009/0048556 and 2009/0149800) disclose a drug delivery system including a pair of electrodes coupled to drug reservoirs 24 controlled by a microprocessor 12. The microprocessor may be programmed through a wireless signal receiver.

Notwithstanding the forgoing, there remains a need for an effective, simple, non-invasive and non-surgical process and system utilizing a disposable patch for treating wrinkles and fine lines.

There also remains a need for a process and system utilizing a disposable patch for wrinkle reduction which may be manufactured at low-cost and high volume.

There also remains a need for a process and system utilizing a disposable patch for wrinkle reduction with precision timing of delivery of active ingredients.

There also remains a need for an apparatus having an adhesive disposable patch with a plurality of active ingredients, a power supply, and a controller in communication with the power supply controlling current using a ramping current profile.

SUMMARY OF INVENTION

The present invention is directed to a process or method of use and a system for wrinkle reduction.

The system includes a patch assembly applied and adhesively secured to the skin of the consumer. Each patch assembly includes a substantially planar top sheet and a substantially planar substrate. Connectors or snaps pass through the top sheet and substrate. On the substrate is a layer of a chemical composition including active ingredients and an adhesive in order to adhere to the skin.

The patch assembly or assemblies are connectable to a detachable electronic locket assembly. The locket assembly may include a housing to form an enclosure. Within the enclosure of the housing is a battery which powers a microprocessor based controller or printed circuit board (PCB). The controller is wired to a pair of electrodes through wires to a wiring harness. The housing, the battery and the controller are suspended from the wiring harness.

In order to use the present invention, the patch assembly or assemblies are positioned and aligned on the skin so that the chemical composition is in contact with and applied to the skin. A pair of electrodes are connected to the connectors or snaps of the patch assembly.

A current is applied from the locket assembly through the electrodes into the chemical composition of the patch assembly for a selected time period. The active ingredients of the chemical composition are propelled into the skin of the consumer in order to relax the skin. After a selected period of time, the current is stopped and the patch assembly is removed.

The patch assembly may then be disconnected from the locket assembly. The patch assembly may thereafter be discarded and the locket assembly may be reused.

BRIEF DESCRIPTION OF THE DRAWINGS

FIG. 3A is a patch assembly of a second preferred embodiment while

DETAILED DESCRIPTION OF THE PREFERRED EMBODIMENTS

The embodiments discussed herein are merely illustrative of specific manners in which to make and use the invention and are not to be interpreted as limiting the scope of the present invention.

While the invention has been described with a certain degree of particularity, it is to be noted that many modifications may be made in the details of the invention's construction and the arrangement of its components without departing from the spirit and scope of this disclosure. It is understood that the invention is not limited to the embodiments set forth herein for purposes or exemplification.

The present invention includes at least two preferred embodiments—a first preferred embodiment utilized on the skin surrounding the eyes of a consumer and a second preferred embodiment utilized on the forehead and bridge of the nose of a consumer.

Figure 1:
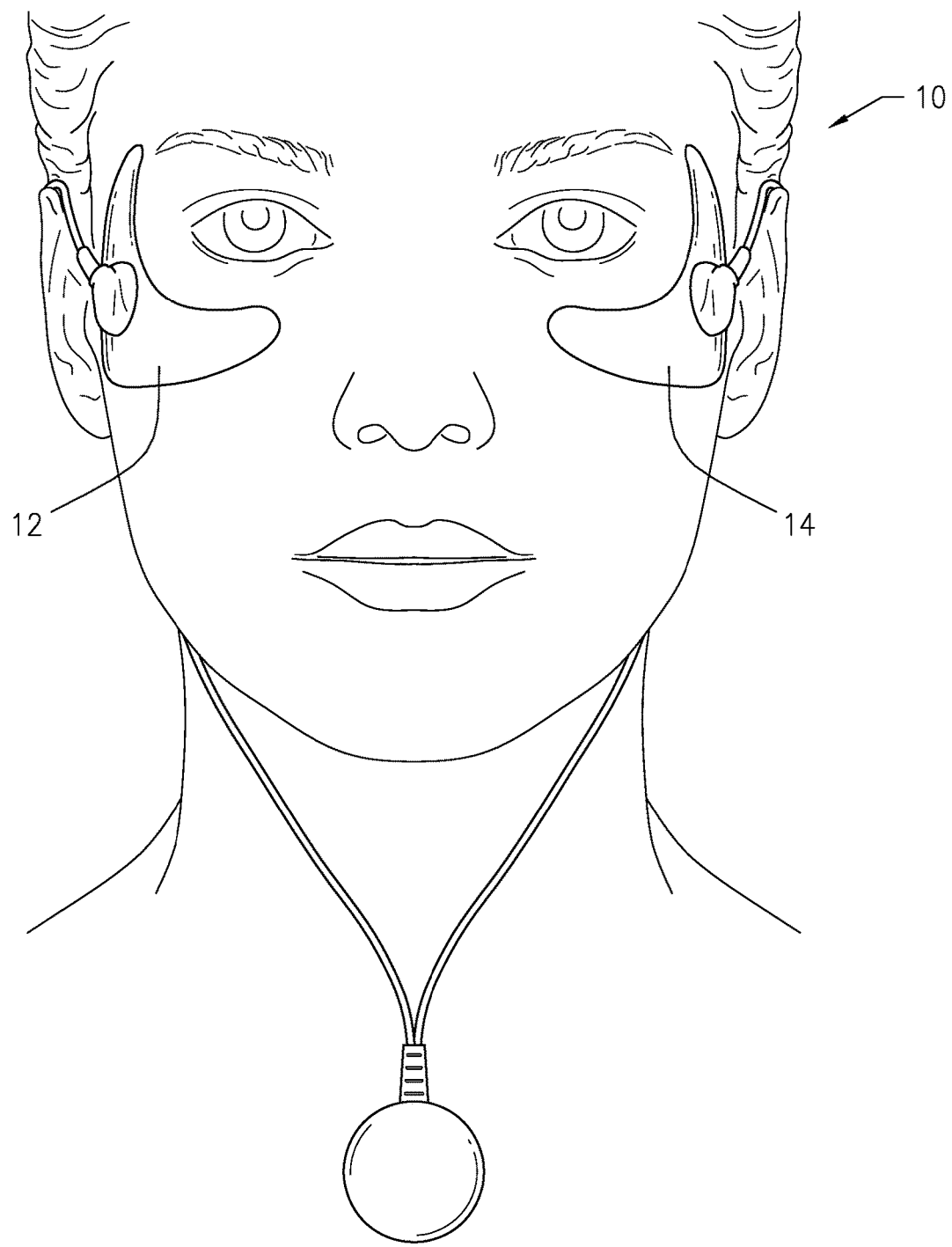
FIG. 1 is an illustration of a first preferred embodiment of a process and system for iontophoretic wrinkle reduction in accordance with the present invention.

Referring to the drawings in detail, FIG. 1 is an illustration of the first preferred embodiment 10 of the present invention surrounding the eyes of a consumer. As will be described herein in detail, a pair of patch assemblies 12 and 14 are applied and adhesively secured to the skin of a consumer surrounding the eyes.

Figure 2A:
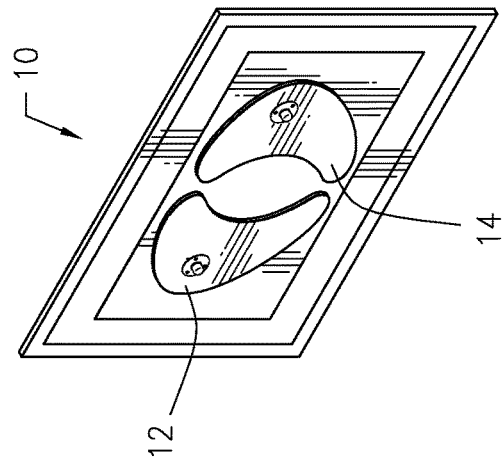
FIG. 2A illustrates a prospective view and FIG. 2B is an exploded view of patch assemblies of the first preferred embodiment of the present invention.
Figure 2B:
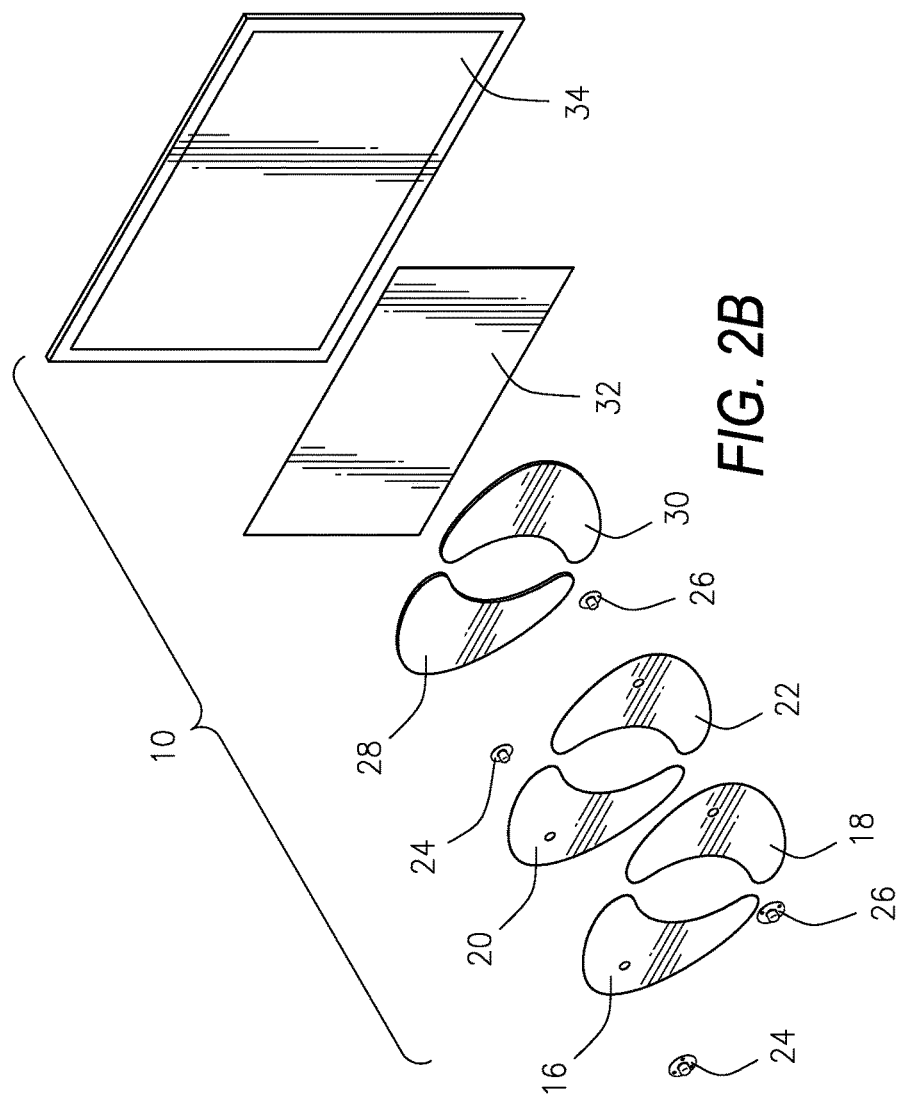

FIG. 2A illustrates a perspective view of the patch assemblies 12 and 14 prior to use and FIG. 2B is an exploded view of the patch assemblies 12 and 14 illustrating the components thereof.

Each of the patch assemblies 12 and 14 may include a substantially planar top sheet 16 and 18, respectively. The patch assemblies 12 and 14 may also include a substantially planar substrate 20 and 22, respectively.

The top sheet 16 and 18 and the substrates 20 and 22 each have holes or apertures which are aligned in order to receive conductive connectors or snaps 24 and 26 that pass therethrough. Each of the connectors or snaps may be in two-part form. In one non-limiting example, known type electromechanical connectors may be utilized.

Adjacent and on the substrates 20 and 22 are layers of a chemical composition, which may be in the nature of a hydrogel 28 and 30, respectively. The hydrogel 28 and 30 will contain active ingredients of the chemical composition and may also include an adhesive in order to adhere to the skin. The active ingredients may include hyaluronic acid, stressed yeast cell lysate, yeast cell derivative, and cross-linked synthetically derived protein. The hyaluronic acid may be in the range of 0.1 to 15%.

The hydrogel 28 and 30 are in fluid communication with the connections or snaps 24 and 26. Accordingly, current or voltage delivered to the connectors or snaps is delivered to the hydrogel. Alternatively or additionally, carbon ink may be added to the substrate layers to improve the conductivity of the electrode assembly.

The patch assemblies 12 and 14 may be stored and transported on a release liner sheet 32. The patch assemblies may be easily peeled off or removed from the liner sheet. The entire assemblies and the liner sheet 32 may be stored in a pouch 34.

Figure 3A:
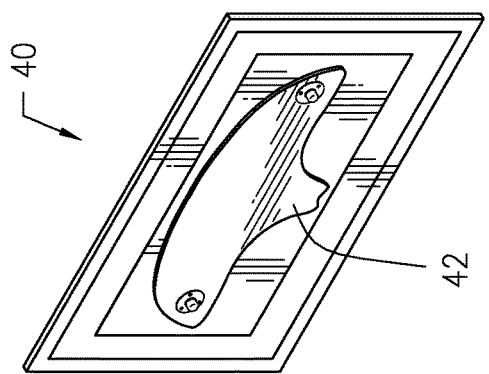
Figure 3B:
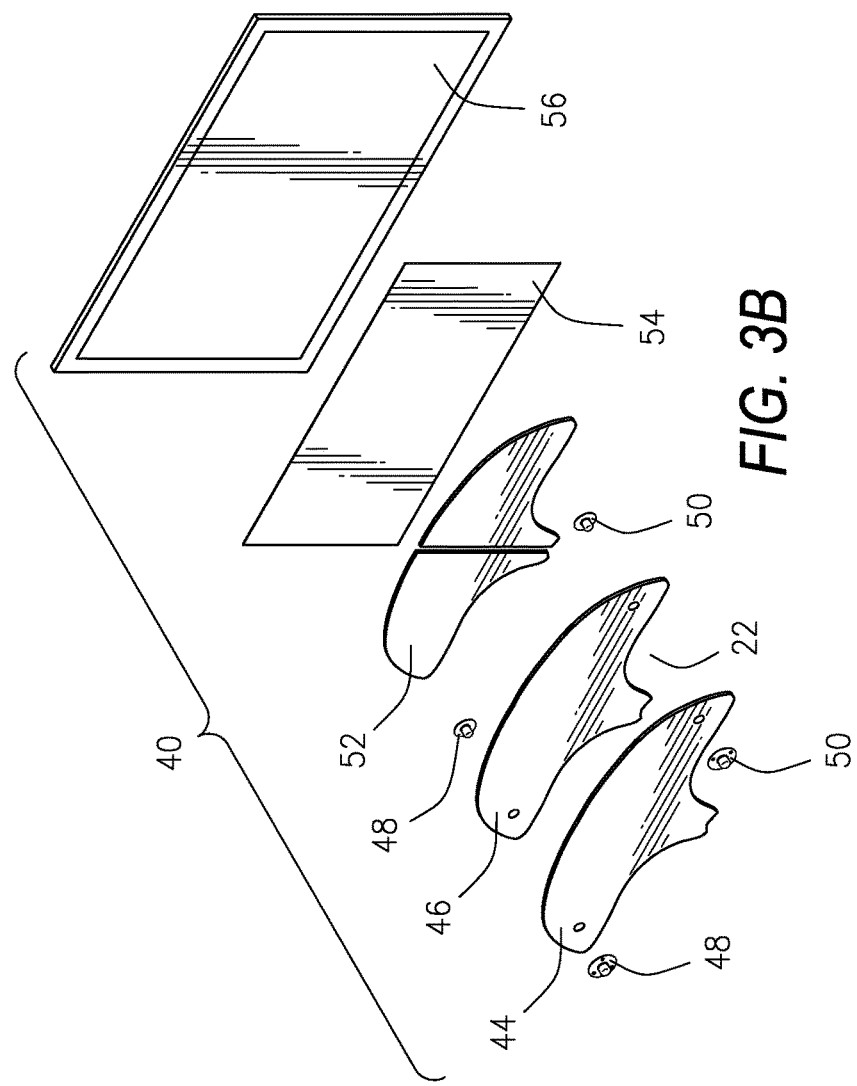
FIG. 3B is an exploded view of the patch assembly shown in FIG. 3A.

A second preferred embodiment of the present invention to be applied to the forehead and bridge of the nose is shown in assembled form in FIG. 3A and is shown exploded in FIG. 3B.

The second preferred embodiment includes a patch assembly 42 shown fully assembled in FIG. 3A prior to use. The patch assembly 42 may include a substantially planar top sheet 44 and an aligned substantially planar substrate 46. The top sheet 44 and substrate 46 each include aligned holes or apertures to receive a pair of connectors or snaps 48 and 50.

The patch assembly includes a layer of chemical composition in the hydrogel 52. The entire patch assembly 42 may be transported and stored on a liner sheet 54. The patch assembly 42 and the liner sheet may be stored in a pouch 56.

In a preferred arrangement, the patch assemblies are disposable after use. In each embodiment, the patch assemblies are connectable to an electronic locket assembly 60.

Figure 4:
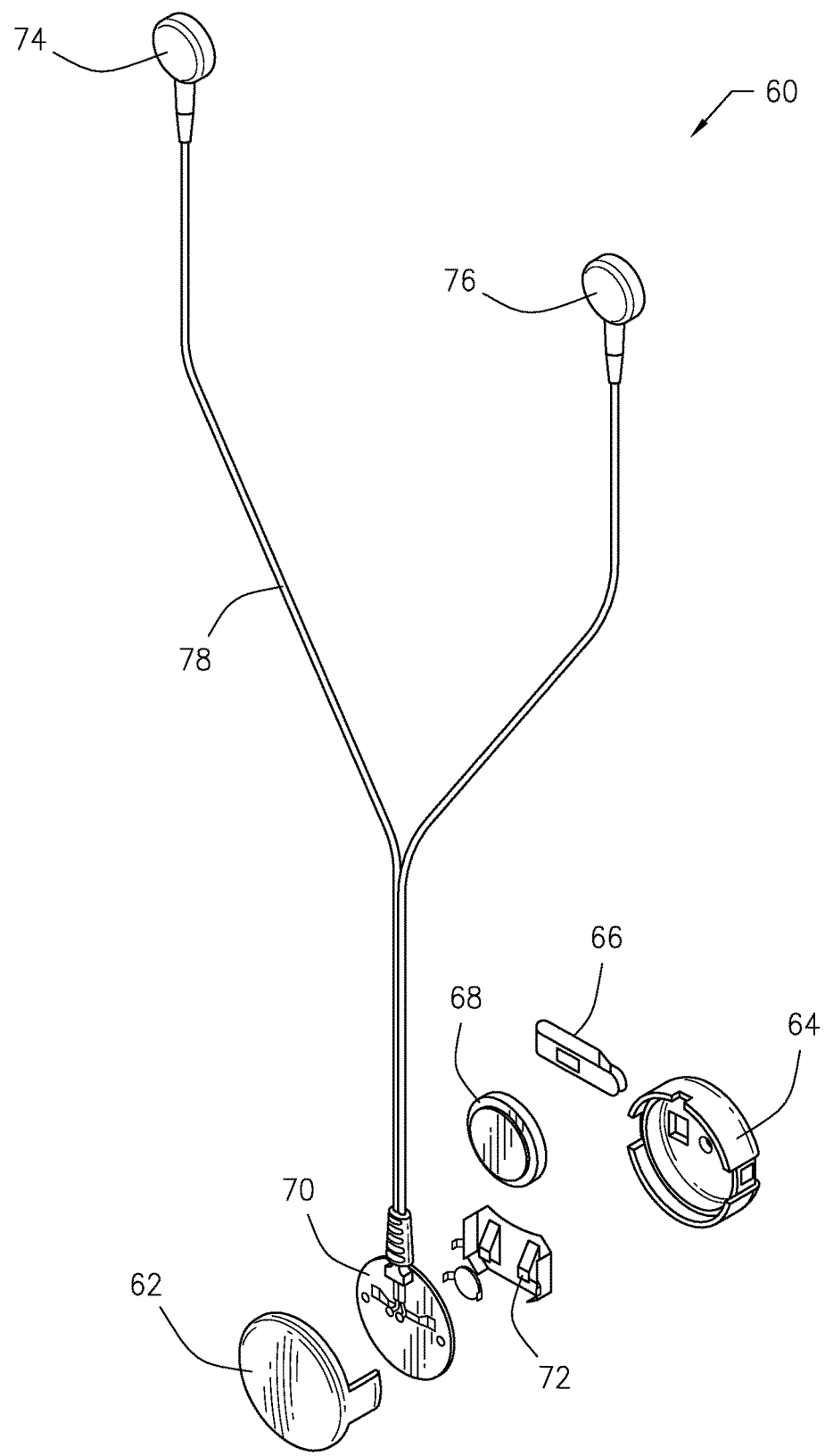
FIG. 4 illustrates an exploded view of an electronic locket assembly utilized in connection with the present invention.
Figure 5D:
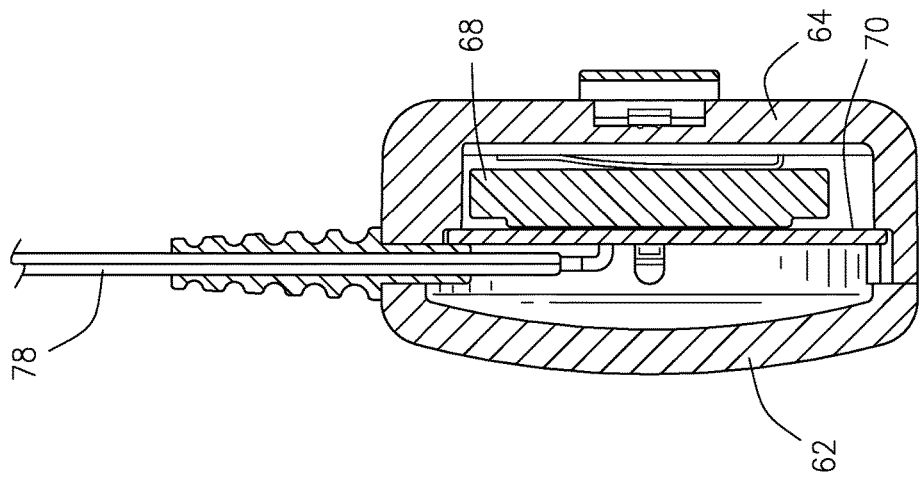
FIG. 5D is a sectional view taken through section line D-D of FIG. 5A.
Figure 5C:
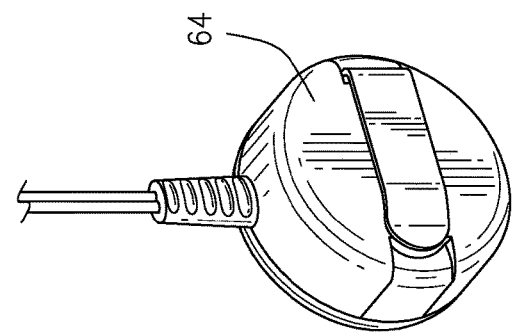
FIGS. 5A, 5B and 5C show alternate views of the lock assembly shown in FIG. 4.
Figure 5A:
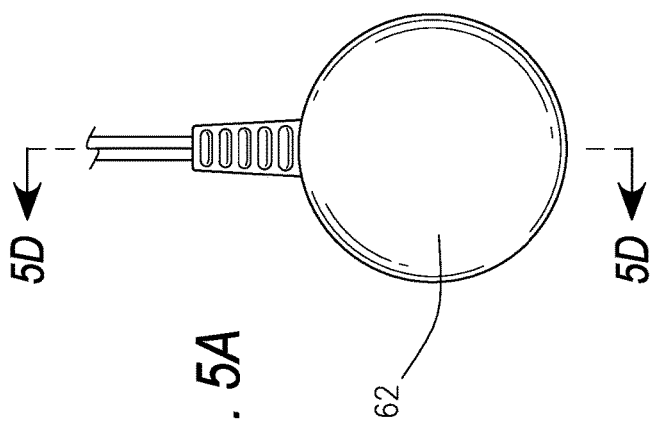
Figure 5B:
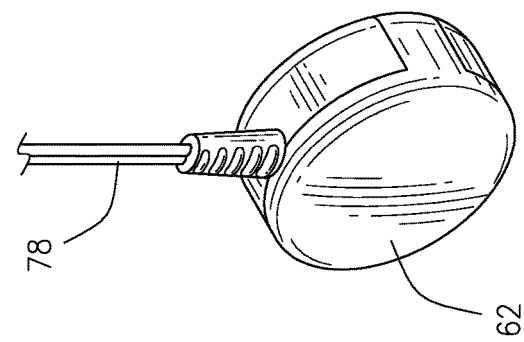

FIG. 4 illustrates an exploded view of the electronic locket assembly 60. FIGS. 5A, 5B and 5C show alternate views of the locket assembly 60 with FIG. 5D illustrating a sectional view taken through section line D-D of FIG. 5A. The locket assembly 60 may include a front housing 62 which mates with a rear housing 64 to form an enclosure. Attached to the housing may be an optional clasp or clip 66. Within the enclosure of the housing is a battery 68 which powers a microprocessor based controller or printed circuit board (PCB) 70. A contact or contacts 72 connect the battery 68 to the controller 70.

The microprocessor based controller 70 is, in turn, wired to a pair of electrodes 74 and 76 through wires or a wiring harness 78.

The housing 62 and 64, the battery 68 and controller 70 may hang from or be suspended from the wiring harness 78.

The process and system of the present invention uses iontophoresis as the motive force for transdermal delivery of a defined amount of active ingredients.

In order to use the system of the present invention, initially, the patch assembly or assemblies are removed from the storage pouch and removed from the liner sheet and then positioned and aligned on the skin so that the chemical composition is in contact with and applied to the skin. The adhesive in the chemical composition serves to removably secure the patch assembly to the skin.

The pair of electrodes 74 and 76 are connected to the connectors or snaps of the patch assembly either in advance of application to the skin or after application. The process is continued by electronically activating the patch assembly.

Figure 7:
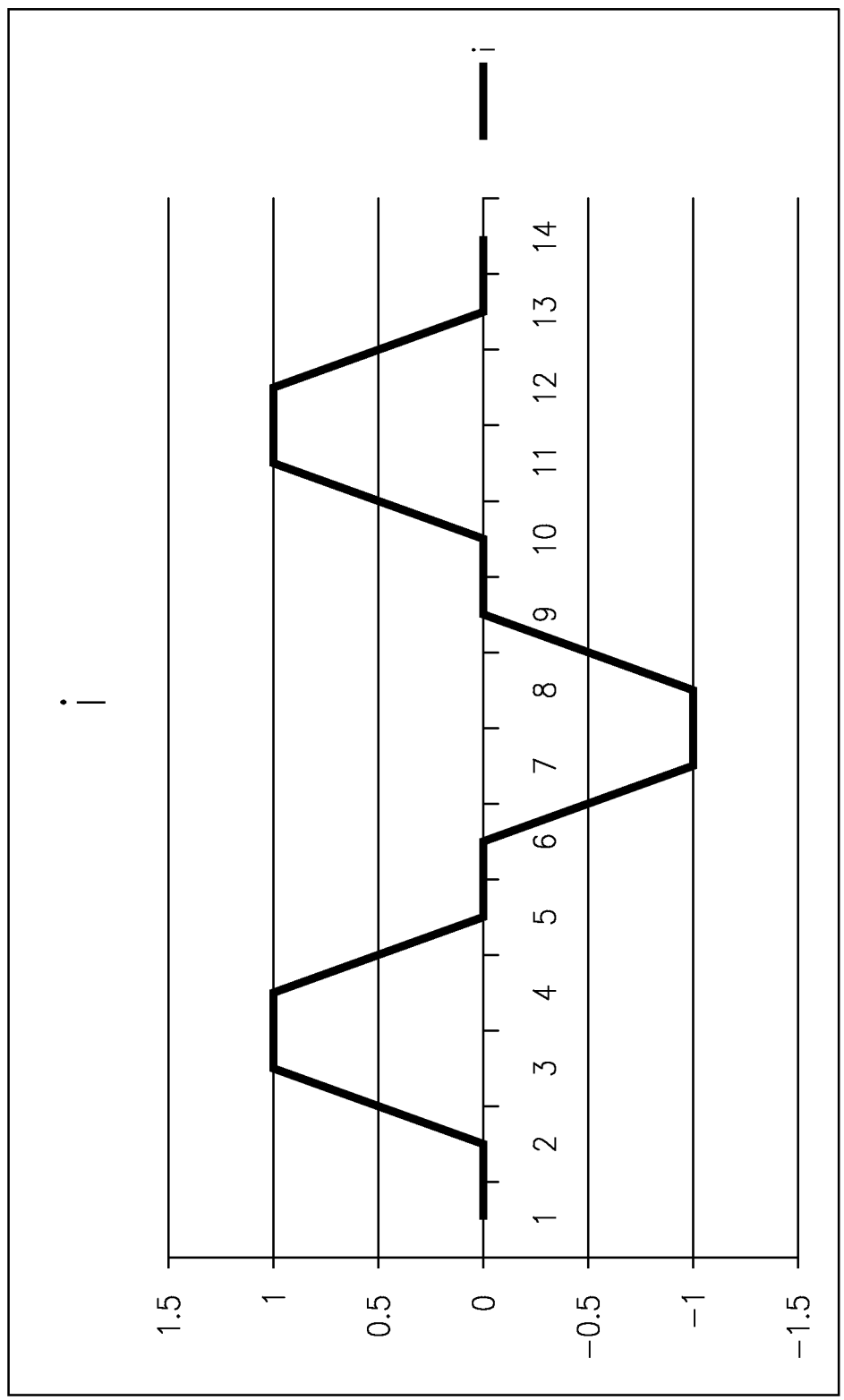
FIG. 7 illustrates a schematic representation of delivery of the electric current cycle during usage of the present invention.

Thereafter, a current is applied from the locket assembly 60 through the electrodes 74 and 76 into the chemical composition of the patch assembly for a selected time period. The active ingredients of the chemical composition are propelled into the skin of the consumer in order to relax the skin or achieve other beneficial results. After a selected period of time, the current optionally may be reversed at least twice, for example as illustrated in FIG. 7. Eventually, the current is stopped and the patch assembly is removed from the skin. The patch assembly may be disconnected from the locket assembly 60. The patch assembly may thereafter be discarded.

As an additional step or measure, after the patch assembly is removed, any residue of the chemical composition may be massaged into the skin. The procedure may be periodically repeated.

Figure 6:
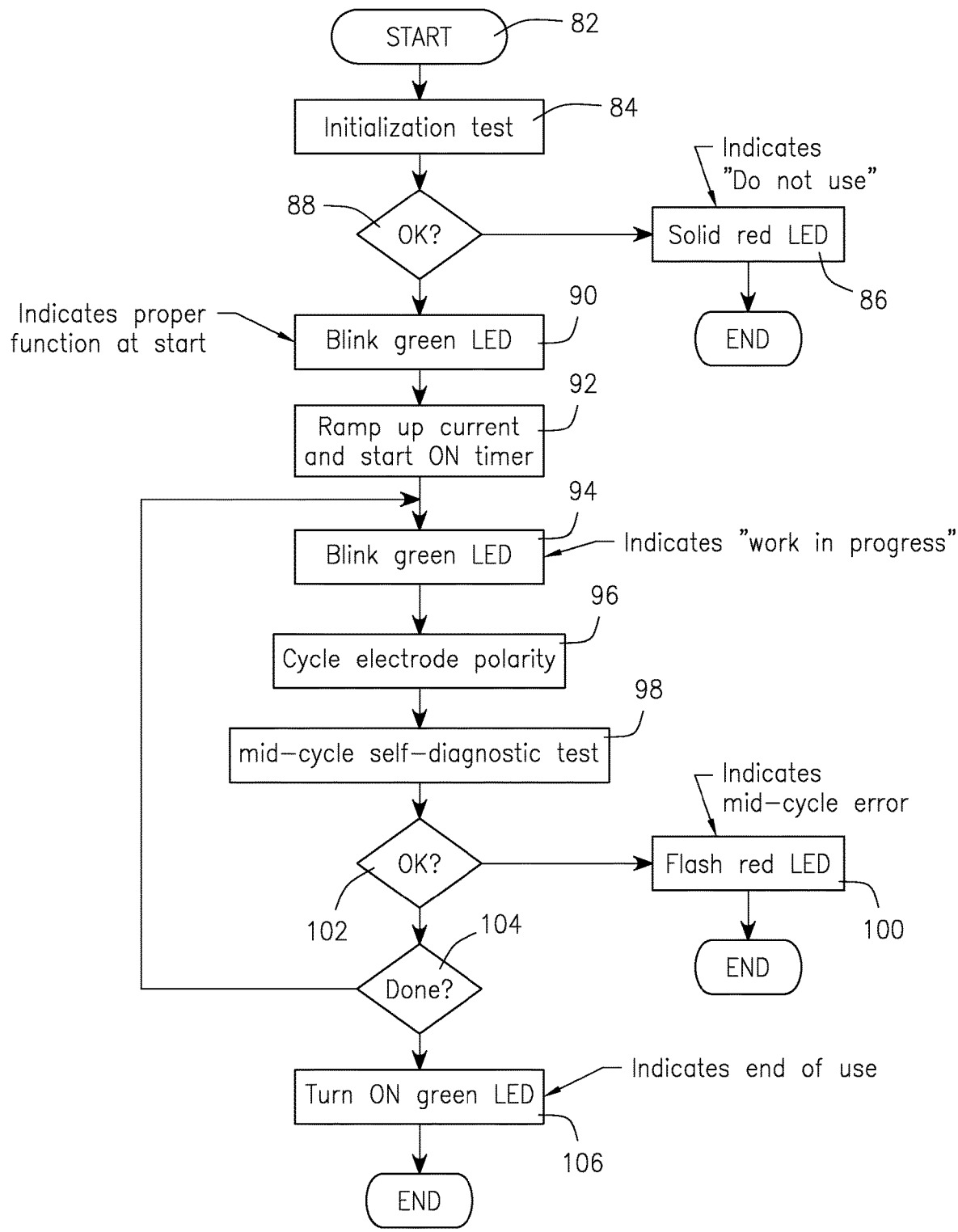
FIG. 6 is a diagrammatic flow chart of the process or method of application of the present invention.

FIG. 6 illustrates a diagrammatic, flow chart of the process or method of application of the current during the delivery cycle of the invention. After start of the procedure, as shown in Box 82, the microprocessor based controller 70 will conduct a self initialization test as shown in Box 84. The process can be started conventionally by a button or switch or may be activated by a change in resistance between the electrodes triggered by skin contact.

If the initialization test does not result in an affirmative outcome, a solid red LED or other indicator will be provided as shown at Box 86 and the device will not be used. If the initialization test is satisfactory, as shown in Diamond 88, proper functioning will be indicated by a green LED as shown at Box 90.

Current to the device will be permitted to ramp up and a timer will be started as shown at Box 92. While the current is being delivered through the chemical composition and into the skin, a blinking green LED will be employed, as shown at Box 94.

The polarity of the current will be cycled or alternated as shown at Box 96. FIG. 7 illustrates a schematic representation of the current cycle. The current will be ramped up and then held for a time period. During the time period, the power supply and the controller 70 are configured to apply no current through the electrodes 74 and 76. Thereafter, the current will be ramped down and the polarity changed.

Additionally, a mid-cycle self diagnostic test may be performed by the controller as shown at box 98. If an error is detected, a red LED will be displayed as shown at Box 100 and the procedure will be terminated. If the diagnostic test is satisfactory, as shown at Diamond 102, the procedure will be continued until the time period is completed as shown at Diamond 104. When the time period has been completed, the green light ceases to blink and remains on for a period of time to indicate the end of the procedure as shown at Box 106.

Thereafter, the patch assembly is removed from the skin and the locket assembly 60 is detached from the patch assembly. The locket assembly may be reused.

If at any time after the cycle has started, one of the electrodes or patch assemblies falls off, an error condition is signaled. If not reconnected within a reasonable time, the system defaults to an off position.

Whereas, the present invention has been described in relation to the drawings attached hereto, it should be understood that other and further modifications, apart from those shown or suggested herein, may be made within the spirit and scope of this invention.

What is claimed is:

1. An apparatus comprising:
   (a) a patch comprising (i) a hydrogel comprising one or more active ingredients and (ii) an adhesive;
   (b) a first electrode in communication with the hydrogel;
   (c) a second electrode in communication with the hydrogel;
   (d) a power supply in communication with the first electrode and the second electrode; and
   (e) a controller in communication with the power supply, the first electrode, and the second electrode;
   wherein the power supply and controller are configured to apply an iontophoretic current through the first electrode and the second electrode for a selected time period and to reverse the polarity of the iontophoretic current at least twice during the selected time period, the iontophoretic current being held at a fixed current level for a predetermined time interval between each reversal of polarity.

2. The apparatus of claim 1, wherein the active ingredients comprise hyaluronic acid.

3. The apparatus of claim 2, wherein the hydrogel comprises 0.1%-15% hyaluronic acid.

4. The apparatus of claim 3, wherein the hydrogel comprises 0.6%-15% hyaluronic acid.

5. The apparatus of claim 1, wherein the apparatus further comprises a timer.

6. The apparatus of claim 1, wherein the controller is configured to activate the power supply by sensing a change in electrical resistance between the electrodes.

7. The apparatus of claim 1, wherein the power supply comprises a battery.

8. The apparatus of claim 1, wherein at least one of the active ingredients is selected from the group consisting of a yeast cell lysate, a yeast cell derivative, and a cross-linked synthetically derived protein.

9. The apparatus of claim 1, wherein the iontophoretic current is reversed to an equal magnitude but opposite polarity at least twice during the selected time period.

10. The apparatus of claim 1, wherein the power supply and the controller are configured to apply no current through the first electrode and the second electrode during the predetermined time interval.

11. An apparatus comprising:
    (a) a first patch comprising (i) a first hydrogel comprising a first active ingredient and (ii) an adhesive;
    (b) a second patch comprising (i) a second hydrogel comprising a second active ingredient and (ii) an adhesive;
    (c) a first electrode in communication with the first hydrogel;
    (c) a second electrode in communication with the second hydrogel;
    (d) a power supply in communication with the first electrode and the second electrode; and
    (e) a controller in communication with the power supply, the first electrode, and the second electrode;
    wherein the power supply and controller are configured to apply an iontophoretic current through the first electrode and the second electrode for a selected time period and to reverse the polarity of the iontophoretic current at least twice during the selected time period, the iontophoretic current being held at a fixed current level for a predetermined time interval between each reversal of polarity.

12. The apparatus of claim 11, wherein the first active ingredient, the second active ingredient, or both comprises hyaluronic acid.

13. The apparatus of claim 12, wherein the first hydrogel, the second hydrogel, or both comprises 0.1%-15% hyaluronic acid.

14. The apparatus of claim 11, wherein the apparatus further comprises a timer.

15. The apparatus of claim 11, wherein the controller is configured to activate the power supply by sensing a change in electrical resistance between the electrodes.

16. The apparatus of claim 11, wherein the power supply comprises a battery.

17. The apparatus of claim 11, wherein at least one of the active ingredients is selected from the group consisting of a yeast cell lysate, a yeast cell derivative, and a cross-linked synthetically derived protein.

18. The apparatus of claim 11, wherein the iontophoretic current is reversed to an equal magnitude but opposite polarity at least twice during the selected time period.

19. The apparatus of claim 11, wherein the power supply and the controller are configured to apply no current through the first electrode and the second electrode during the predetermined time interval.

20. The apparatus of claim 11, wherein the fixed current level of the iontophoretic current is a zero current level.

\* \* \* \* \*